US009360458B2

(12) United States Patent
Shibata et al.

(10) Patent No.: US 9,360,458 B2
(45) Date of Patent: Jun. 7, 2016

(54) ROTARY TRANSFORMER FOR ROTARY ULTRASONIC TESTING APPARATUS AND ROTARY ULTRASONIC TESTING APPARATUS USING THE SAME

(75) Inventors: Shoji Shibata, Tokyo (JP); Yoichi Fujikake, Tokyo (JP); Kunihiko Hatabara, Tokyo (JP); Michiaki Ishihara, Hyogo (JP); Sohken Mitsui, Hyogo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 289 days.

(21) Appl. No.: 14/111,781

(22) PCT Filed: Apr. 13, 2012

(86) PCT No.: PCT/JP2012/060097
§ 371 (c)(1),
(2), (4) Date: Dec. 24, 2013

(87) PCT Pub. No.: WO2012/141279
PCT Pub. Date: Oct. 18, 2012

(65) Prior Publication Data
US 2014/0102202 A1    Apr. 17, 2014

(30) Foreign Application Priority Data

Apr. 15, 2011    (JP) ................... 2011-091299

(51) Int. Cl.
*G01N 29/24* (2006.01)
*G01N 29/04* (2006.01)
*H01F 38/18* (2006.01)

(52) U.S. Cl.
CPC .............. *G01N 29/04* (2013.01); *G01N 29/043* (2013.01); *H01F 38/18* (2013.01); *G01N 2291/044* (2013.01); *G01N 2291/2634* (2013.01)

(58) Field of Classification Search
CPC ................ G01N 29/04; G01N 29/043; G01N 2291/044; G01N 2291/2634; H01F 38/18
USPC .................. 73/632, 660, 661, 866.5
See application file for complete search history.

(56) References Cited

U.S. PATENT DOCUMENTS 2,978,651 A * 4/1961 Canada ..................... H03J 3/00
                                                      331/170
4,939,400 A * 7/1990 Matsushita ............. H01F 38/18
                                                      310/208

(Continued)

FOREIGN PATENT DOCUMENTS

JP         58-48200        3/1983
JP         05-101953       4/1993

(Continued)

*Primary Examiner* — Laura Martin
*Assistant Examiner* — Rose M Miller
(74) *Attorney, Agent, or Firm* — Clark & Brody (57) ABSTRACT

The rotary transformer 5 includes a plate-shaped stator 51 having a coil arranged on one surface thereof, and a plate-shaped rotator 52 having a coil arranged on one surface thereof, in which the respective coil-arranged surfaces are disposed to face with each other so that signal transmission in a frequency range of 1 to 10 MHz is performed between the coils. The stator includes a substrate 512 on which a plurality of one-turn coils are formed into a concentric shape, and a supporting member 513. The rotator includes a substrate 522 on which one-turn coils 521 of same number are formed into a concentric shape, and a supporting member 523. Air or a material M which is an insulator and has a relative magnetic permeability substantially equal to 1 is lying between the substrate 512 and the supporting member 513, and between the substrate 522 and the supporting member 523.

4 Claims, 8 Drawing Sheets

(56) References Cited

U.S. PATENT DOCUMENTS

| | | | | |
|---|---|---|---|---|
| 5,594,176 | A * | 1/1997 | Kiefer | G01N 29/0672 324/238 |
| 2010/0244816 | A1 * | 9/2010 | Nakamura | G01B 7/30 324/207.25 |
| 2010/0321007 | A1 * | 12/2010 | Fukuda | G01D 5/2093 324/207.25 |
| 2011/0043196 | A1 * | 2/2011 | Fujita | G01D 5/2046 324/207.16 |
| 2011/0075796 | A1 * | 3/2011 | Loef | A61B 6/56 378/15 |

FOREIGN PATENT DOCUMENTS

| | | |
|---|---|---|
| JP | 6-94685 | 4/1994 |
| JP | 6-242081 | 9/1994 |
| JP | 7-12783 | 1/1995 |
| JP | 7-37736 | 2/1995 |
| JP | 7-201612 | 8/1995 |
| JP | 2002-345822 | 12/2002 |
| JP | 2004-344247 | 12/2004 |

* cited by examiner

Figure 1
PRIOR ART

Ultrasonic flaw detector 3

ROTARY TRANSFORMER FOR ROTARY ULTRASONIC TESTING APPARATUS AND ROTARY ULTRASONIC TESTING APPARATUS USING THE SAME

TECHNICAL FIELD

The present invention relates to a rotary transformer for a rotary ultrasonic testing apparatus, and a rotary ultrasonic testing apparatus using the same. In particular, the present invention relates to a rotary transformer for a rotary ultrasonic testing apparatus which is excellent in transmission efficiency of signal even when transmitting a signal for use in rotary ultrasonic testing, and a rotary ultrasonic testing apparatus using the same.

BACKGROUND ART

Conventionally, there is known a rotary ultrasonic testing apparatus whereby testing is performed while an ultrasonic probe is rotated along the circumferential direction of a test material having a tubular or bar shape.

Figure 1:
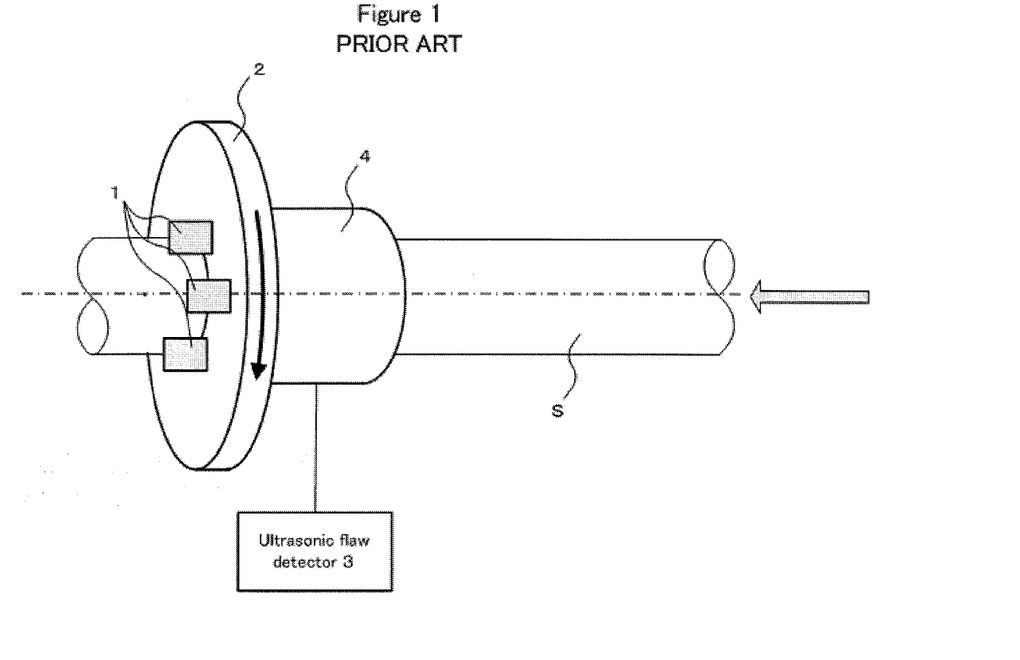
FIG. 1 is a schematic view to show an outline configuration of a typical rotary ultrasonic testing apparatus.

As shown in FIG. 1, a typical rotary ultrasonic testing apparatus includes: an ultrasonic probe 1 for transmitting/receiving ultrasonic wave to/from a test material S; a probe holder 2 which, with the ultrasonic probe 1 attached thereto, is adapted to rotate in the circumferential direction of the test material S; an ultrasonic flaw detector 3 for controlling the transmitting/receiving of ultrasonic wave to/from the ultrasonic probe 1 and testing the test material S based on an echo received at the ultrasonic probe 1; and a signal transmission section 4 for transmitting a signal between the ultrasonic probe 1 and the ultrasonic flaw detector 3.

In the rotary ultrasonic testing apparatus having the above described configuration, by moving the test material S straight in the longitudinal axial direction and rotating the probe holder 2, and therefore the ultrasonic probe 1 (at around 50 to 2000 rpm), the trajectory of the ultrasonic probe 1 will become a spiral-shape on the surface of the test material S, thereby allowing a rapid testing throughout the entire cross section of the test material S.

Here, known methods for transmitting a signal in a frequency range (1 to 10 MHz) typically used for ultrasonic testing in the signal transmission section 4 include methods of using (1) a slip ring, (2) a capacitive coupling, and (3) a rotary transformer. These methods will now be described one by one.

(1) Method of Using a Slip Ring (See, for Example, Patent Literature 1)

Figure 2:
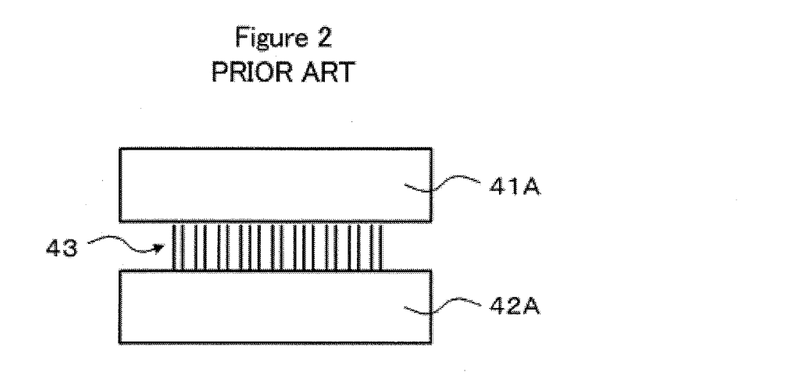
FIG. 2 is an explanatory diagram to illustrate a method of transmitting a signal used in ultrasonic testing, by using a slip ring.

In this method, as shown in FIG. 2, a stationary-side electrode 41A and a rotating-side electrode 42A are provided in the signal transmission section 4 (see FIG. 1). A brush 43 is provided between the stationary-side electrode 41A and the rotating-side electrode 42A. The stationary-side electrode 41A is electrically connected with the ultrasonic flaw detector 3 (see FIG. 1). On the other hand, the rotating-side electrode 42A is electrically connected with the ultrasonic probe 1 (see FIG. 1) and adapted to rotate integrally with the ultrasonic probe 1 (the probe holder 2) (see FIG. 1).

Accordingly, the stationary-side electrode 41A and the rotating-side electrode 42A are brought into contact via the brush 43 to cause signal transmission between the ultrasonic probe 1 and the ultrasonic flaw detector 3.

Since this method is based on a contact scheme, a problem is that it is not suitable for high-speed rotation and its maintainability is very low.

(2) Method of Using a Capacitive Coupling (See, for Example, Patent Literature 2)

Figure 3:
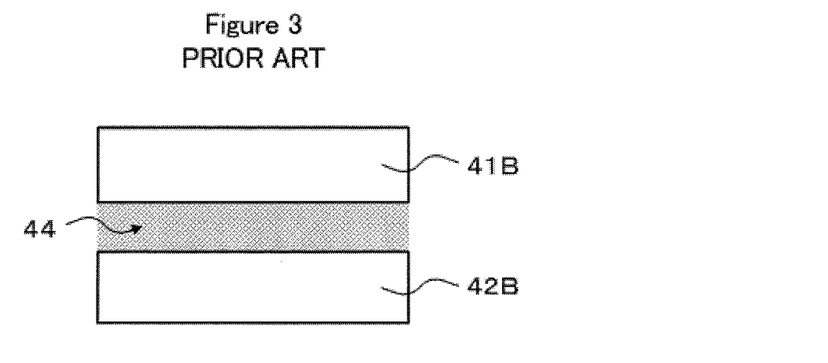
FIG. 3 is an explanatory diagram to illustrate a method of transmitting a signal used in ultrasonic testing, by using a capacitive coupling.

In this method, as shown in FIG. 3, a stationary-side electrode 41B and a rotating-side electrode 42B are provided in the signal transmission section 4 (see FIG. 1). A dielectric substance 44 such as air and water is retained between the stationary-side electrode 41B and the rotating-side electrode 42B. The stationary-side electrode 41B is electrically connected with the ultrasonic flaw detector 3 (see FIG. 1). On the other hand, the rotating-side electrode 42B is electrically connected with the ultrasonic probe 1 and adapted to rotate integrally with the ultrasonic probe 1 (the probe holder 2) (see FIG. 1).

Thus, as described above, signal transmission between the ultrasonic probe 1 and the ultrasonic flaw detector 3 is achieved by the dielectric substance 44 being retained between the stationary-side electrode 41B and the rotating-side electrode 42B, thereby forming a capacitor.

When air is used as the dielectric substance 44, this method has a problem of poor maintainability since the transmission efficiency of the air is small, and therefore the distance between the electrodes needs to be very small (about 0.1 to 0.5 mm).

On the other hand, in the method of using a capacitive coupling, when water is used as the dielectric substance 44, it is necessary to retain water uniformly although the distance between electrodes can be fairly large (about 2 mm).

Figure 4:
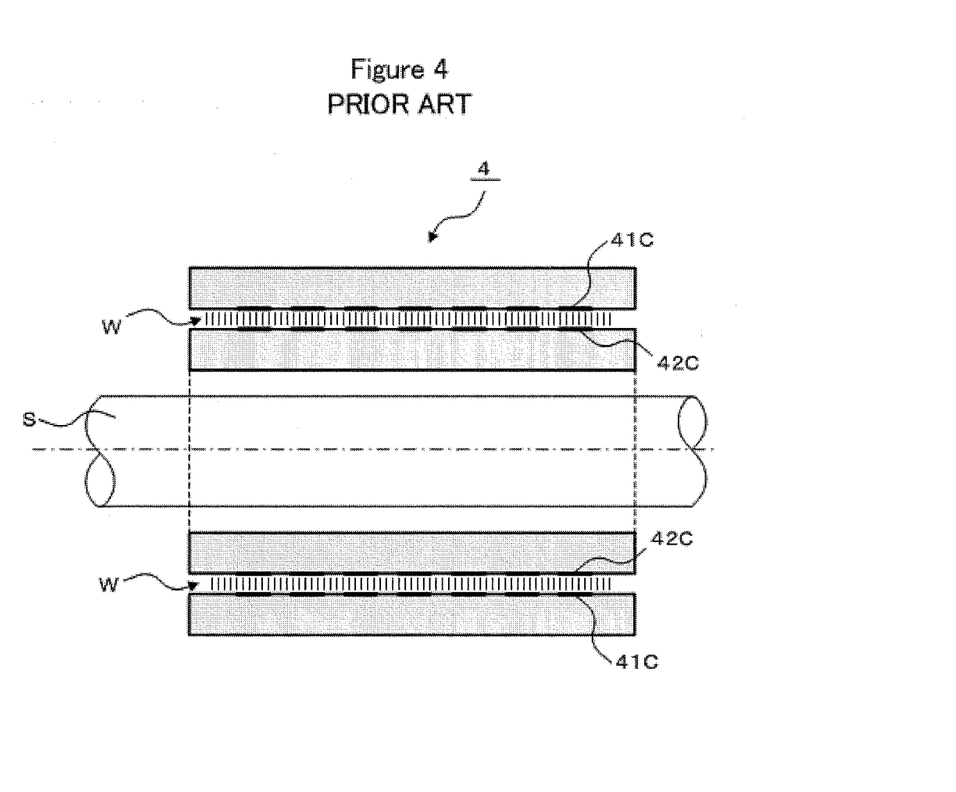
FIG. 4 is an explanatory diagram to illustrate a method of transmitting signals used in ultrasonic testing through multiple channels, by using a capacitive coupling.

When multi-channel signal transmission is performed (a plurality of ultrasonic probes 1 are provided), in order to retain water W uniformly, it is necessary to arrange a plurality of stationary-side electrodes 41C and the rotating-side electrodes 42C in the longitudinal direction of the test material S, as shown in FIG. 4. For this reason, the length of the signal transmission section 4 increases in the longitudinal direction of the test material S, thus leading to an upsizing of the ultrasonic testing apparatus. Moreover, if the diameter of the test material S increases, the diameter of the signal transmission section 4 also increases, making it more difficult to retain water W.

(3) Method of Using a Rotary Transformer (See, for Example, Patent Literature 3)

Figure 5:
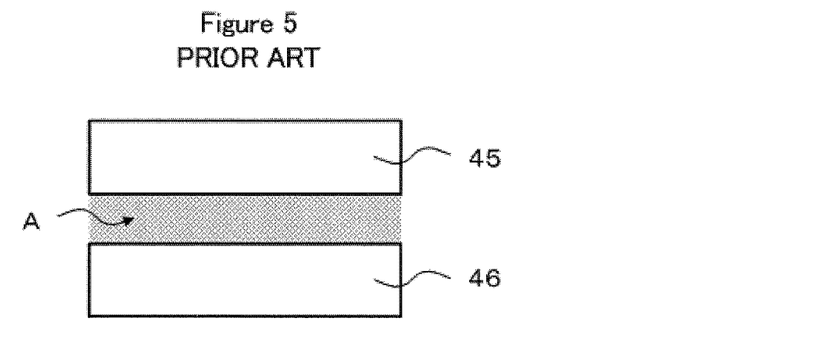
FIG. 5 is an explanatory diagram to illustrate a method of transmitting a signal used in ultrasonic testing, by using a rotary transformer.

In this method, as shown in FIG. 5, a stationary-side coil 45 and a rotating-side coil 46 are provided in the signal transmission section 4 (see FIG. 1). The stationary-side coil 45 is electrically connected with the ultrasonic flaw detector 3 (see FIG. 1). On the other hand, the rotating-side coil 46 is electrically connected with the ultrasonic probe 1, and adapted to rotate integrally with the ultrasonic probe 1 (the probe holder 2) (see FIG. 1).

Thus, signal transmission between the ultrasonic probe 1 and the ultrasonic flaw detector 3 is performed through electromagnetic induction generated between the stationary-side coil 45 and the rotating-side coil 46.

This method is advantageous in that air A may be provided between the coils, and moreover the distance between the coils can be large unlike the above described method of using a capacitive coupling.

However, since the rotary transformer which is formerly proposed for the signal transmission section 4 of the rotary ultrasonic testing apparatus takes on a form in which a plurality of stationary-side coils 45 and a plurality of rotating-side coils 46 are arranged in the longitudinal direction of the test material S in the same manner as with the above described stationary-side electrode 41C and the rotating-side electrode 42C when performing multi-channel signal transmission (a plurality of ultrasonic probes 1 are provided), a problem is that the length of the signal transmission section 4 increases in the longitudinal direction of the test material S, thereby leading to an upsizing of the ultrasonic testing apparatus.

Here, as the rotary transformer, there is known a plate-type rotary transformer, including a plate-shaped stator having a coil arranged on one surface thereof, and a plate-shaped rotator having a coil arranged on one surface thereof, in which the respective coil-arranged surfaces of the stator and the rotator are disposed to face with each other, so that a signal is transmitted between the coils facing with each other (see, for example, Patent Literatures 4 and 5).

It is expected that applying the above described plate-type rotary transformer as that for the signal transmission section of the rotary ultrasonic testing apparatus will suppress upsizing of the ultrasonic testing apparatus even when multi-channel signal transmission is performed. That is, it is expected that adopting a configuration in which a plurality of coils are arranged for each of the stator and rotator constituting the plate-type rotary transformer, and the test material is inserted through a central hole of the plate-type rotary transformer will reduce the length of the signal transmission section in the longitudinal direction of the test material, thereby allowing to suppress upsizing of the ultrasonic testing apparatus.

CITATION LIST

Patent Literature

[Patent Literature 1] JP6-94685A
[Patent Literature 2] JP7-12783A
[Patent Literature 3] JP6-242081A
[Patent Literature 4] JP7-201612A
[Patent Literature 5] JP7-37736A

SUMMARY OF INVENTION

Technical Problem

A stator and a rotator constituting a conventional plate-type rotary transformer are generally configured such that a groove is formed in the plate-shaped substrate made up of a ferromagnetic material such as soft ferrite to increase the transmission efficiency of the signal, and a coil is arranged in the groove. Alternatively, a substrate made of an electric conductor such as aluminum may be used instead of a substrate made of ferromagnetic material. In either case, configuration is such that the coil and the substrate are in direct contact (mechanical contact) contact with each other.

However, when transmitting a signal in a frequency range of about 1 to 10 MHz and having a voltage of about 100 to 500 V which is typically used in ultrasonic testing by using such plate-like rotary transformer, a problem is that the transmission efficiency declines due to the effects of hysteresis loss in the ferromagnetic material constituting the substrate, and eddy-current loss in the electric conductor constituting the substrate.

The present invention has been made to solve the above described problems of conventional arts, and has its object to provide a rotary transformer for a rotary ultrasonic testing apparatus which is excellent in transmission efficiency of signal even when transmitting a signal for use in rotary ultrasonic testing, and a rotary ultrasonic testing apparatus using the same.

Solution to Problem

In order to achieve the object, the present invention provides a rotary transformer for a rotary ultrasonic testing apparatus, comprising a plate-shaped stator having a coil arranged on one surface thereof, and a plate-shaped rotator having a coil arranged on one surface thereof, the respective coil-arranged surfaces of the stator and the rotator being disposed to face with each other so that signal transmission in a frequency range of 1 to 10 MHz is performed between the coils facing with each other, wherein the stator comprises a substrate on which a plurality of one-turn coils are formed into a concentric shape, and a supporting member for supporting the substrate; the rotator comprises a substrate on which one-turn coils of same number as that of the one-turn coils formed in the stator are formed into a concentric shape, and a supporting member for supporting the substrate; and air or a material which is an insulator and has a relative magnetic permeability substantially equal to 1 is lying between the substrate and the supporting member included in the stator, and between the substrate and the supporting member included in the rotator.

The stator and the rotator included in a rotary transformer for a rotary ultrasonic testing apparatus relating to the present invention include a substrate formed with a coil, and a supporting member for supporting the substrate, and air or a material which is an insulator and has a relative magnetic permeability substantially equal to 1 (for example, plastic such as Bakelite) is lying between the substrate and the supporting member. In other words, the coil and the supporting member are not in direct contact (mechanical contact) with each other, and a material which is less prone to induce electromagnetic field lies between the coil and the supporting member. As a result of this, even if the supporting member is formed of a ferromagnetic material such as soft ferrite or a conductor such as aluminum, the electromagnetic field induced by the coil is less likely to be attenuated in the supporting member, and a decline of transmission efficiency is less likely to occur.

Here, in general, the transmission efficiency increases in proportional to the number of turns of the coil. However, in a frequency range (1 to 10 MHz) which is typically used in ultrasonic testing, when the number of turns of the coil increases and thereby the length of the coil wire increases, the stray capacitance between coil wires increases, resulting in an increase in impedance. Since a signal source for driving the coil is considered to be a constant voltage power supply in an instantaneous sense, if impedance increases as described above, the current flowing in the coil will be attenuated, and thereby the transmission efficiency between the coil formed in the stator and the coil formed in the rotator will be dramatically reduced.

Therefore, a plurality of one-turn coils are formed in the stator and the rotator included in the rotary transformer for a rotary ultrasonic testing apparatus relating to the present invention. Thus, since using one-turn coils will cause the stray capacitance between coil wires to become zero, there will be no decline in transmission efficiency.

As described so far, according to the present invention, it is possible to obtain a rotary transformer for a rotary ultrasonic testing apparatus which is excellent in transmission efficiency of signal even when transmitting a signal for use in ultrasonic testing.

Here, when a plurality of coils are arranged to transmit a plurality of different signals, a problem of interference (cross talk) between respective signals may arise. To avoid this, conventionally, a shielding electrode for screening electromagnetic field is provided (see, for example, Patent Literature 5). However, in a frequency range (1 to 10 MHz) which is typically used in ultrasonic testing, providing the shielding electrode in proximity to the coil will lead to a problem that transmission efficiency declines due to the wire stray capacitance between the coil and the electrode.

Therefore, preferably, the plurality of one-turn coils formed in the substrate included in each of the stator and the rotator are formed into a concentric shape with a spacing substantially equal to the coil width therebetween.

According to such preferable configuration, it is possible to reduce cross talk between signals transmitted in each one-turn coil.

Preferably, a separation distance between the substrate and the supporting member included in each of the stator and the rotator is 5 to 10 times as large as a gap between the one-turn coils formed in the stator and the one-turn coils formed in the rotator.

If the separation distance between the substrate and the supporting member is less than 5 times the gap between both the one-turn coils, electromagnetic field induced by the one-turn coil may undesirably be attenuated in the supporting member, thereby causing a decline in transmission efficiency. On the other hand, if the separation distance between the substrate and the supporting member exceeds 10 times the gap between both the one-turn coils, since the effect of the attenuation of electromagnetic field by the supporting member decreases, the thickness of the rotary transformer will simply end up with an increase of the thickness of the rotary transformer, even when the separation distance is excessively increased.

In order to achieve the object, the present invention also provides a rotary ultrasonic testing apparatus, comprising: the rotary transformer for a rotary ultrasonic testing apparatus according to any of claims 1 to 3; a plurality of ultrasonic probes which are electrically connected with the plurality of one-turn coils formed in the rotator, and which rotate integrally with the rotator; and an ultrasonic flaw detector which is electrically connected with the plurality of one-turn coils formed in the stator.

According to a rotary ultrasonic testing apparatus relating to the present invention, it is possible to efficiently perform multiple-channel signal transmission while suppressing upsizing of the apparatus.

Advantageous Effects of Invention

According to a rotary ultrasonic testing apparatus relating to the present invention, transmission efficiency of signal is excellent even when transmitting a signal for use in ultrasonic testing. Also, according to a rotary ultrasonic testing apparatus relating to the present invention, it is possible to efficiently perform multiple-channel signal transmission while suppressing upsizing of the apparatus.

DESCRIPTION OF EMBODIMENTS

An embodiment of the present invention will now be described with reference to the appended drawings.

Figure 6A:
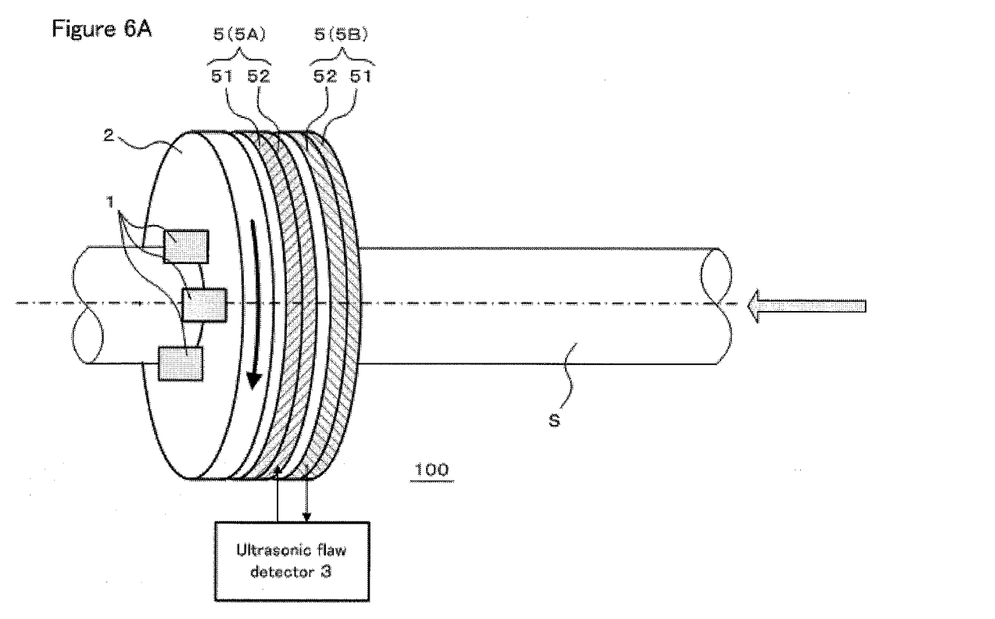
FIGS. 6A and 6B are schematic views to show an outline configuration of a rotatory ultrasonic testing apparatus relating to an embodiment of the present invention.
Figure 6B:
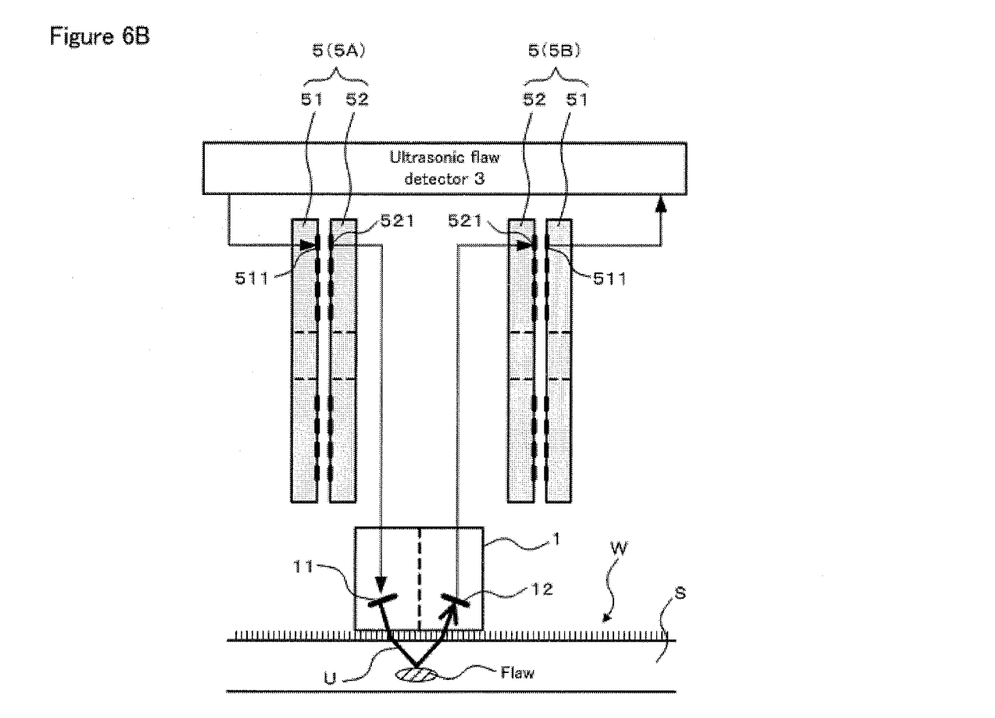

FIGS. 6A and 6B are schematic views to show an outline configuration of a rotatory ultrasonic testing apparatus relating to an embodiment of the present invention. FIG. 6A is a diagram to show a general configuration of the apparatus, and FIG. 6B is a diagram to explain the relation of electric connection for one ultrasonic probe.

As shown in FIG. 6, a rotary ultrasonic testing apparatus 100 relating to the present embodiment includes: a plurality of ultrasonic probes 1 for transmitting/receiving ultrasonic wave to/from a test material S; a probe holder 2 which, with the ultrasonic probes 1 attached thereto, is adapted to rotate in the circumferential direction of the test material S; an ultrasonic flaw detector 3 for controlling the transmitting/receiving of ultrasonic wave to/from the ultrasonic probe 1 and testing the test material S based on an echo received at the ultrasonic probe 1; and a rotary transformer 5 for a rotary ultrasonic testing apparatus (hereinafter also simplify referred to as a rotary transformer) for transmitting a signal between the ultrasonic probe 1 and the ultrasonic flaw detector 3. The test material S is inserted through a central hole of the probe holder 2 and the rotary transformer 5.

The rotary transformer 5 is configured to include a plate-shaped stator 51 having a coil arranged on one surface thereof, and a plate-shaped rotator 52 having a coil arranged on one surface thereof, the respective coil-arranged surfaces of the stator 51 and the rotator 52 being disposed to face with each other so that signal transmission in a frequency range of 1 to 10 MHz is performed between the coils facing with each other. The rotary ultrasonic testing apparatus 100 relating to the present embodiment includes a pair of rotary transformers 5 (a transmitting rotary transformer 5A and a receiving rotary transformer 5B).

Figure 7A:
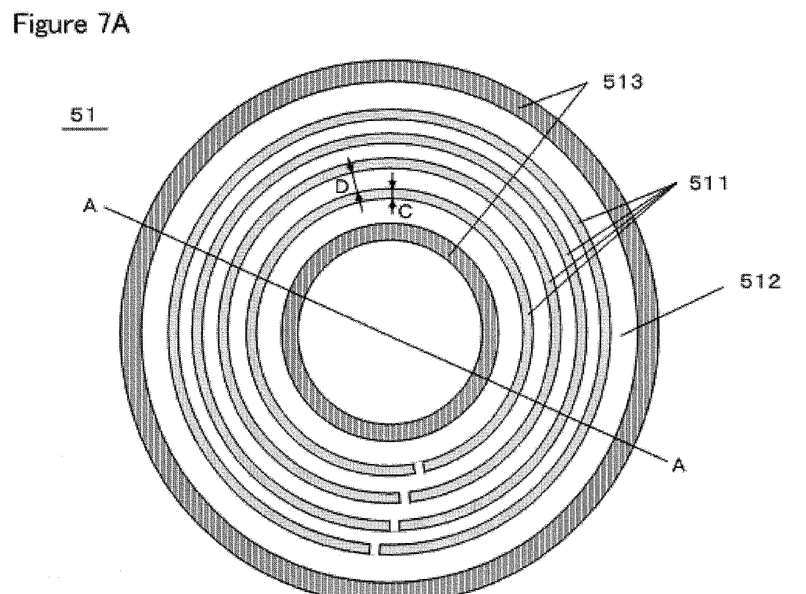
FIGS. 7A and 7B are schematic views to show an outline configuration of a stator included in a rotatory transformer for a rotary ultrasonic testing apparatus relating to an embodiment of the present invention.
Figure 7B:
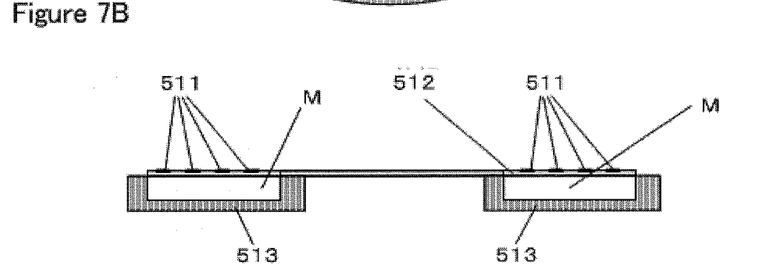

FIGS. 7A and 7B are schematic views to show an outline configuration of the stator 51 included in the rotatory transformer 5. FIG. 7A is a plan view, and FIG. 7B is a cross sectional view taken along the line A-A shown in FIG. 7A.

As shown in FIG. 7, the stator 51 includes a substrate 512 in which a plurality of (four in the example shown in FIGS. 7A and 7B) one-turn coils 511 are formed into a concentric shape, and a supporting member 513 for supporting the substrate 512. The supporting member 513 supports the surface opposite the coil-forming surface of the substrate 512. The supporting member 513 of the present embodiment is formed of aluminum.

Air or a material M which is an insulator and has a relative magnetic permeability substantially equal to 1 (for example, plastic such as Bakelite) is lying between the substrate 512 included in the stator 51 and the supporting member 513. In the example shown in FIGS. 7A and 7B, the cross section of the supporting member 513 is formed into a U-shape such that the region of the substrate 512 where the coils 511 are formed and the supporting member 513 are separated in the thickness direction of the substrate 512, and air is lying between the substrate 512 and the supporting member 513.

The present embodiment is preferably configured such that a plurality of one-turn coils 511, which are formed in the substrate 512 included in the stator 51, are formed into a concentric shape with a spacing D substantially equal to the coil width C therebetween.

Figure 8A:
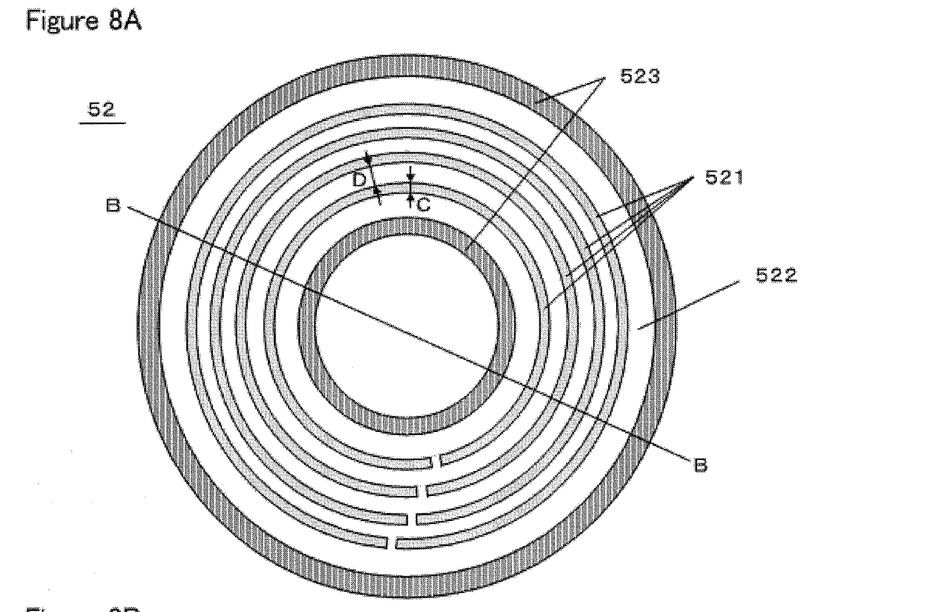
FIGS. 8A and 8B are schematic views to show an outline configuration of a rotator included in a rotatory transformer for a rotary ultrasonic testing apparatus relating to an embodiment of the present invention.
Figure 8B:
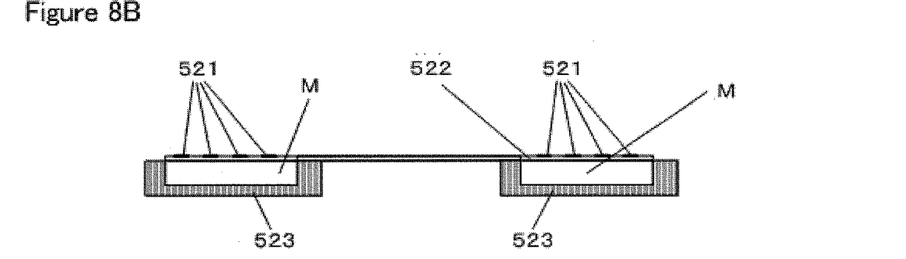

FIGS. 8A and 8B are schematic views to show an outline configuration of a rotator 52 included in the rotary transformer 5. FIG. 8A is a plan view, and FIG. 8B is a cross sectional view taken along the line B-B shown in FIG. 8A.

As shown in FIGS. 8A and 8B, the rotator 52 also includes a substrate 512 in which a plurality of (four in the example shown in FIGS. 8A and 8B) one-turn coils 521 are formed into a concentric shape, and a supporting member 523 for supporting the substrate 522. The supporting member 523 supports the surface opposite the coil-forming surface of the substrate 522. The supporting member 523 is formed of aluminum.

Air or a material M which is an insulator and has a relative magnetic permeability substantially equal to 1 (for example, plastic such as Bakelite) is lying between the substrate 522 included in the rotator 52 and the supporting member 523. In the example shown in FIGS. 8A and 8B, the cross section of the supporting member 523 is formed into a U-shape such that the region of the substrate 522 where the coils 521 are formed and the supporting member 523 are separated in the thickness direction of the substrate 522, and air lies between the substrate 522 and the supporting member 523.

The present embodiment is preferably configured such that a plurality of one-turn coils 521, which are formed in the substrate 522 included in the rotator 52, are formed into a concentric shape with spacing D substantially equal to the coil width C therebetween.

As shown in FIGS. 6A and 6B, the ultrasonic probe 1 of the present embodiment is configured to be an ultrasonic probe of a double crystal probe (transmitting/receiving separate type) which includes a transmitting transducer (transmitter) 11 and a receiving transducer (receiver) 12. The ultrasonic probe 1 is electrically connected with the one-turn coil 521 formed in the rotator 52, and configured to rotate integrally with the rotator 52. To be specific, the transmitter 11 of the ultrasonic probe 1 is electrically connected with the one-turn coil 521 formed in the rotator 52 of the transmitting rotary transformer 5A, and the receiver 12 is electrically connected with the one-turn coil 521 formed in the rotator 52 of the receiving rotary transformer 5B. Thus, the rotator 52 of the transmitting rotary transformer 5A and the rotator 52 of the receiving rotary transformer 5B are configured to rotate integrally with the probe holder 2, so that the rotator 52 of the transmitting rotary transformer 5A and the rotator 52 of the receiving rotary transformer 5B integrally rotate in the circumferential direction of the test material S by the probe holder 2 being rotated in the circumferential direction of the test material S by a predetermined driving source.

As shown in FIGS. 6A and 6B, the ultrasonic flaw detector 3 is electrically connected with the one-turn coil 511 formed in the stator 51. In the present embodiment, the ultrasonic flaw detector 3 is electrically connected with the one-turn coil 511 formed in the stator 51 of the transmitting rotary transformer 5A and the one-turn coil 511 formed in the stator 51 of the receiving rotary transformer 5B.

It is noted that although FIG. 6B shows an example in which one ultrasonic probe 1 is electrically connected with a pair of one-turn coils 521 (a one-turn coil 521 formed in the rotator 52 of the transmitting rotary transformer 5A and a one-turn coil 521 formed in the rotator 52 of the receiving rotary transformer 5B), another ultrasonic probe 1 will be electrically connected with another pair of one-turn coils 521. Moreover, although FIG. 6B shows an example in which the ultrasonic flaw detector 3 is electrically connected with one pair of one-turn coils 511 (a one-turn coil 511 formed in the stator 51 of the transmitting rotary transformer 5A and a one-turn coil 511 formed in the stator 51 of the receiving rotary transformer 5B), it will be electrically connected with another pair of one-turn coils 511 depending on the number of the ultrasonic probes 1.

Further, in the present embodiment, although description has been made on an example in which an ultrasonic probe 1 of a double crystal probe including a transmitter 11 and a receiver 12 is used, the present invention will not be limited to this, and it is possible to use an ultrasonic probe of a single crystal probe in which one transducer is used for both transmitting and receiving. In this case, as the rotary transformer 5, it is not necessary to use a pair of rotary transformers 5 (a transmitting rotary transformer 5A and a receiving rotary transformer 5B), and a single rotary transformer 5 may be used.

When performing ultrasonic testing of a test material S by using a rotary ultrasonic testing apparatus 100 having the above described configuration, the test material S is moved straight in the longitudinal axial direction of the test material S, and the probe holder 2, therefore the ultrasonic probe 1 is rotated. At this time, a signal for causing ultrasonic wave to be transmitted from the transmitter 11 is outputted from the ultrasonic flaw detector 3, and is conveyed to the transmitter 11 via the one-turn coils 511 and 521 of the transmitting rotary transformer 5A. Thereby, the ultrasonic wave U transmitted from the transmitter 11 enters into the test material S via the water W as the contact medium, and an echo thereof will be detected by the receiver 12. The echo detected by the receiver 12 is converted into an electrical signal, and inputted into the ultrasonic flaw detector 3 via the one-turn coils 521 and 511 of the receiving rotary transformer 5B. The ultrasonic flaw detector 3 tests the test material S based on the inputted signal. Since the trajectory of the ultrasonic probe 1 will become a spiral shape on the outer surface of the test material S, it is possible to perform testing throughout the entire cross section of the test material S.

Evaluation tests conducted on the rotary ultrasonic testing apparatus 100 relating to the present embodiment will now be described.

<Evaluation Test Relating to the Separation Distance Between the Substrate and the Supporting Member>

In the rotary ultrasonic testing apparatus 100 relating to the present embodiment, a test for evaluating the echo height from a flaw observed by the ultrasonic flaw detector 3 was performed by appropriately changing both the separation distance between the substrate 512 included in the stator 51 and the supporting member 513, and the separation distance between the substrate 522 included in the rotator 52 and the supporting member 523 for both the transmitting rotary transformer 5A and the receiving rotary transformer 5B.

To be specific, for both the transmitting rotary transformer 5A and the receiving rotary transformer 5B, setting the gap between the coils 511 arranged in the stator 51 and the coils 521 arranged in the rotator 52 to 2 mm, and the thickness of the water W lying between the ultrasonic probe 1 and the test material S to 0.5 mm, testing was performed at a testing frequency of 5 MHz for a flat-bottomed hole having a diameter of 5.6 mm as a flaw. The coils 511 and 521 were one-turn coils having a coil width of 5 mm and the spacing between adjacent coils was 5 mm. It is noted that when a flaw echo was observed, the one-turn coil 511 (diameter: about 1200 mm) arranged on the outermost side of the plurality of one-turn coils 511 was electrically connected with the ultrasonic flaw detector 3. Moreover, the one-turn coil 521 (diameter: about 1200 mm) arranged on the outermost side of the plurality of one-turn coils 521 was electrically connected with the ultrasonic probe 1.

Figure 9:
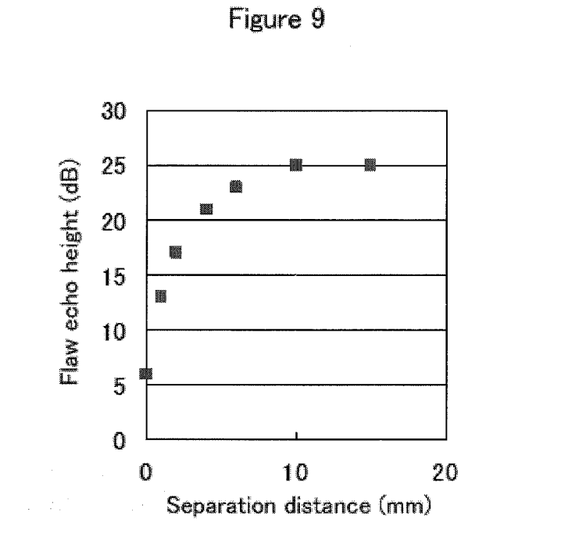
FIG. 9 is a graph to show the result of an evaluation test of the rotary ultrasonic testing apparatus shown in FIGS. 6A and 6B.

FIG. 9 is a graph to show the results of the above described evaluation test.

As shown in FIG. 9, it was revealed that when the substrate 512 (or 522) and the supporting member 513 (or 523) were separated (when air was lying between the substrate and the supporting member), the height of flaw echo became larger compared to when the separation distance was zero (when nothing was lying between the substrate and the supporting member). This is because air which is less prone to induce electromagnetic field was lying between the substrate (coil) and the supporting member so that the electromagnetic field induced by the coil was not likely to be attenuated in the supporting member, and the transmission efficiency was less likely to be reduced even if the supporting member was formed of aluminum which is a conductor as in the present embodiment. To be more specific, the effects of electromagnetic induction between the coil 511 and the supporting member (aluminum) and between the coil 521 and the supporting member (aluminum) decreased so that a decline of the transmission efficiency due to electromagnetic induction between the coil 511 and the coil 521 became less likely to be caused.

Moreover, as shown in FIG. 9, it was revealed that when the separation distance between the substrate and the supporting member was about 10 to 20 mm (about 5 to 10 times as large as the gap of 2 mm between the coils 511 arranged in the stator 51 and the coils 521 arranged in the rotator 52), the observed height of flaw echo became saturation, and the height of flaw echo did not change even if the separation distance was further increased. That is, it was found that even if the separation distance was further increased, there was little effect in suppressing the attenuation in the supporting member, of the electromagnetic field induced by the coil. Therefore, the separation distance between the substrate 512 (or 522) and the supporting member 513 (or 523) is preferably 5 to 10 times as large as the gap between the coils 511 arranged in the stator 51 and the coils 521 arranged in the rotator 52.

<Evaluation Test Regarding the Number of Turns of Coil>

In the rotary ultrasonic testing apparatus 100 relating to the present embodiment, a test for evaluating the echo height from a flaw observed by the ultrasonic flaw detector 3 was performed by appropriately changing the number of turns of the coils formed in the stator 51 and the rotator 52 of the transmitting rotary transformer 5A in a state where the receiving rotary transformer 5B was detached, and the receiving transducer 12 of the ultrasonic probe 1 and the ultrasonic flaw detector 3 were electrically connected in a direct manner.

To be specific, setting the gap between the coils arranged in the stator 51 of the transmitting rotary transformer 5A and the coils arranged in the rotator 52 to 2 mm, the separation distance between the substrate 512 (or 522) and the supporting member 513 (or 523) to 20 mm, and the thickness of the water W lying between the ultrasonic probe 1 and the test material S to 0.5 mm, testing was performed at a testing frequency of 5 MHz for a flat-bottomed hole having a diameter of 5.6 mm as a flaw. Three kinds of coils which were a one-turn coil, a three-turn coil, and a five-turn coil were used as the coils arranged in the transmitting rotary transformer 5A. When the one-turn coil was used, the coil width was 5 mm and the spacing between adjacent coils was 5 mm. When the three-turn coil was used, the coil width was 1 mm, the coil was wound by three turns with a coil width of 1 mm and a gap of 2 mm, and the spacing between adjacent coils was 5 mm. When the five-turn coil was used, the coil was wound by five turns with a coil width of 0.5 mm and a gap of 0.5 mm, and the spacing between adjacent coils was 5 mm. It is noted that when a flaw echo was observed, the coil (diameter: about 1200 mm) arranged on the outermost side of the stator 51 was electrically connected with the ultrasonic flaw detector 3 for any of the one-turn coil, the three-turn coil, and the five-turn coil. Moreover, the coil (diameter: 1200 mm) arranged on the outermost side of the rotator 52 was electrically connected with the ultrasonic probe 1.

Figure 10:
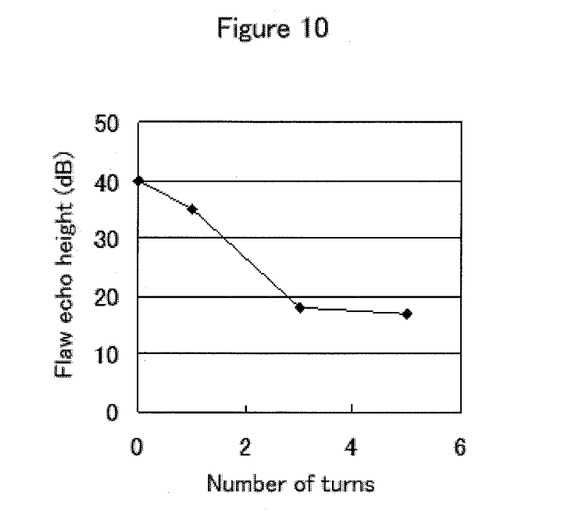
FIG. 10 is a graph to show the result of another evaluation test of the rotary ultrasonic testing apparatus shown in FIGS. 6A and 6B.

FIG. 10 is a graph to show the results of the above described evaluation test. It is noted that in FIG. 10, the data which was plotted at the position where the number of turns was zero shows the result of evaluating the echo height from a flaw which was observed by the ultrasonic flaw detector 3 in a state in which the both the transmitting rotary transformer 5A and the receiving rotary transformer 5B were detached, and the transmitter 11 and the receiver 12 of the ultrasonic probe 1 were electrically connected with the ultrasonic flaw detector 3 in a direct manner.

As shown in FIG. 10, it was revealed that as the number of turns of coil increased, the flaw echo height decreased. This is because when the number of turns of coil increased and thereby the length of the coil became large, the stray capacitance between coil wires became large, thereby increasing impedance, so that the current flowing in the coil was attenuated, thereby decreasing the transmission efficiency between the coil formed in the stator 51 and the coil formed in the rotator 52.

Based on the results described so far, a plurality of one-turn coils 511 and 521 are arranged in the stator 51 and the rotator 52 included in the rotary transformer 5 relating to the present embodiment, as described above.

<Evaluation Test Relating to Coil Spacing>

In the rotary ultrasonic testing apparatus 100 relating to the present embodiment, a test for evaluating the height of an interference echo between adjacent coils observed by the ultrasonic flaw detector 3 was performed by appropriately changing the spacing between a plurality of one-turn coils 511 and 521 formed in the stator 51 and the rotator 52 for both the transmitting rotary transformer 5A and the receiving rotary transformer 5B.

To be specific, for both the transmitting rotary transformer 5A and the receiving rotary transformer 5B, setting the gap between the coils 511 arranged in the stator 51 and the coils 521 arranged in the rotator 52 to 2 mm, the separation distance between the substrate 512 (or 522) and the supporting member 513 (or 523) to 20 mm, and the thickness of the water W lying between the ultrasonic probe 1 and the test material S to 0.5 mm, testing was performed at a testing frequency of 5 MHz for a flat-bottomed hole having a diameter of 5.6 mm as a flaw. The coils 511, 521 were a one-turn coil having a coil width of 5 mm, and the spacing between adjacent coils was changed in a range of 0.5 to 15 mm. It is noted that when an echo from a flaw was observed, the one-turn coil 511 (diameter: about 1200 mm) arranged on the outermost side of the plurality of one-turn coils 511 and the one-turn coil 511 adjacent thereto were electrically connected with the ultrasonic flaw detector 3. Moreover, the one-turn coil 521 (diameter: about 1200 mm) arranged on the outermost side of the plurality of one-turn coils 521 and the one-turn coil 521 adjacent thereto were electrically connected with two of the ultrasonic probes 1. Then, an echo received by the ultrasonic probe 1, which was electrically connected with the one-turn coil 521 arranged on the outermost side, was observed with the ultrasonic flaw detector 3.

Figure 11A:
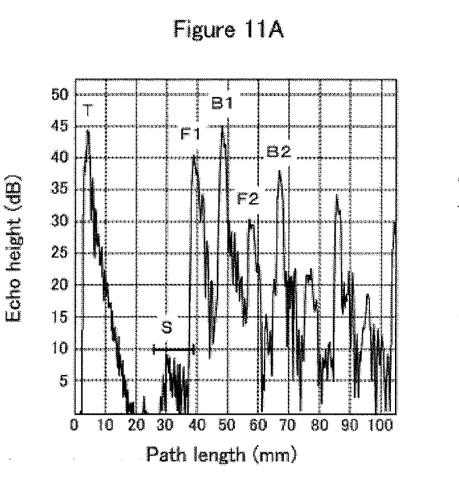
FIGS. 11A and 11B are graphs to show an example of received waveform observed in a further evaluation test of the rotary ultrasonic testing apparatus shown in FIGS. 6A and 6B.
Figure 11B:
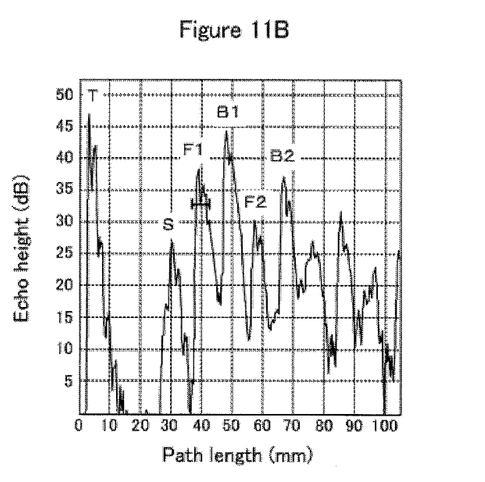

FIGS. 11A and 11B show an example of received waveform observed in the above described evaluation test. FIG. 11A shows an example of received waveform when the spacing between adjacent one-turn coils was 5 mm, and FIG. 11B shows an example of received waveform when the spacing between adjacent one-turn coils was 0.5 mm. It is noted that in FIGS. 11A and 11B, an echo shown by a symbol T is a transmitted echo, an echo shown by a symbol S is a surface echo, an echo shown by a symbol F1 or F2 is a flaw echo, and an echo shown by a symbol B1 or B2 was a bottom echo.

Since the ultrasonic probe 1 of the present embodiment was an ultrasonic probe of double crystal probe including the transmitter 11 and the receiver 12, it was usual that a surface echo (an echo reflected at the surface of the test material S) was scarcely received by the receiving transducer 12. However, when a plurality of one-turn coils are arranged to transmit a plurality of different signals, it is believed that the height of the surface echo S increases due to interference (cross talk) between respective signals. As shown in FIG. 11A, when the spacing between adjacent one-turn coils was set to 5 mm which was substantially equal to the coil width, there was less interference between respective signals, and the height of surface echo S was small. On the other hand, as shown in FIG. 11B, when the spacing between the adjacent one-turn coils was set to 0.5 mm, the height of surface echo S became large due the interference between respective signals. Moreover, although not shown, even when the spacing between adjacent one-turn coils was set to be larger than the coil width, the received waveform showed a large height of the surface echo S. These results have revealed that an optimum value exists for the spacing between adjacent one-turn coils to reduce the height of surface echo.

Figure 12:
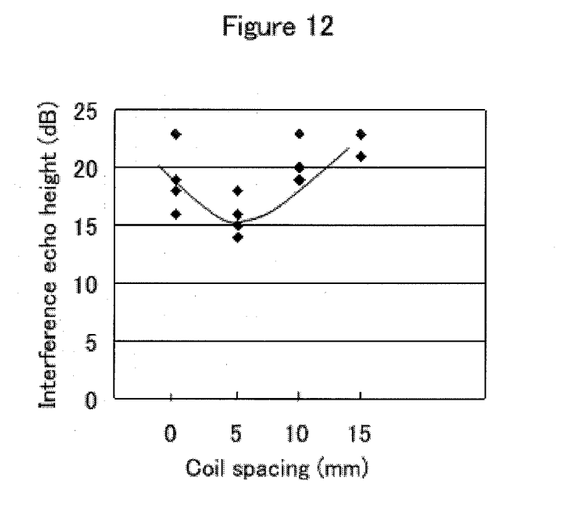
FIG. 12 is a graph to show the height of the interference echo (surface echo) observed in a further evaluation test of the rotary ultrasonic testing apparatus shown in FIGS. 6A and 6B.

FIG. 12 is a graph to show the height of interference echo (surface echo S) observed in the above described evaluation test.

As shown in FIG. 12, it was revealed that setting the spacing between adjacent one-turn coils to 5 mm which is substantially equal to the coil width allows to reduce the height of interference echo, that is, the cross talk between signals transmitted by each one-turn coil.

Based on the above described results, the present embodiment is preferably configured such that a plurality of one-turn coils 511 formed in the substrate 512 included in the stator 51 and a plurality of one-turn coils 521 formed in the substrate 522 included in the rotator 52 are formed into a concentric shape with a spacing substantially equal to the coil width therebetween.

REFERENCE SIGNS LIST

1 Ultrasonic probe
2 Probe holder
3 Ultrasonic flaw detector
5 Rotary transformer
5A Transmitting rotary transformer
5B Receiving rotary transformer
11 Transmitting transducer (transmitter)
12 Receiving transducer (receiver)
51 Stator
52 Rotator
100 Rotary ultrasonic testing apparatus
511 One-turn coil
512 Substrate
513 Supporting member
521 One-turn coil
522 Substrate
523 Supporting member
M Air or a material which is an insulator and has a relative magnetic permeability substantially equal to 1
S Test material

The invention claimed is:

1. A rotary transformer for a rotary ultrasonic testing apparatus, comprising a plate-shaped stator having first coils arranged on one surface thereof, and a plate-shaped rotator having second coils arranged on one surface thereof, the respective coil-arranged surfaces of the stator and the rotator being disposed to face with each other so that signal transmission in a frequency range of 1 to 10 MHz is performed between the first coils and the second coils facing with each other, wherein
the stator comprises a first substrate on which a plurality of one-turn coils as the first coils are formed into a concentric shape, and a first supporting member for supporting the first substrate; and
the rotator comprises a second substrate on which one-turn coils as the second coils of same number as that of the one-turn coils formed in the stator are formed into a concentric shape, and a second supporting member for supporting the second substrate,
and air or a material which is an insulator and has a relative magnetic permeability substantially equal to 1 is lying between the first substrate and the first supporting member included in the stator, and between the second substrate and the second supporting member included in the rotator.

2. The rotary transformer for a rotary ultrasonic testing apparatus according to claim 1, wherein the plurality of one-turn coils formed in the first substrate included in the stator and the plurality of one-turn coils formed in the second substrate included in the rotator are formed into a concentric shape with a spacing substantially equal to the coil width therebetween.

3. The rotary transformer for a rotary ultrasonic testing apparatus according to claim 1, wherein
a separation distance between the first substrate and the first supporting member included in the stator and a separation distance between the second substrate and the second supporting member included in the rotator are 5 to 10 times as large as a gap between the one-turn coils formed in the stator and the one-turn coils formed in the rotator.

4. A rotary ultrasonic testing apparatus, comprising:
the rotary transformer for a rotary ultrasonic testing apparatus according to claim 1;
a plurality of ultrasonic probes which are electrically connected with the plurality of one-turn coils formed in the rotator, and which rotate integrally with the rotator; and
an ultrasonic flaw detector which is electrically connected with the plurality of one-turn coils formed in the stator.

* * * * *